US012698267B2

(12) United States Patent
Cheruku et al.

(10) Patent No.: US 12,698,267 B2
(45) Date of Patent: Aug. 4, 2026

(54) ONE-POT HOMOGENEOUS PROCESS FOR THE LARGE SCALE MANUFACTURE OF 2-SUBSTITUTED BENZIMIDAZOLES

(71) Applicant: ECOLAB USA INC., St. Paul, MN (US)

(72) Inventors: Pradeep Cheruku, Bolingbrook, IL (US); Patricia Gillenwater, Glen Ellyn, IL (US); Nicolas Leflemme, Buffalo Grove, IL (US); Alexander Mantis, Brookfield, IL (US); James Joseph Michels, Sturgis, MI (US); Suresh R. Sriram, Aurora, IL (US)

(73) Assignee: ECOLAB USA Inc., St. Paul, MN (US)

( * ) Notice: Subject to any disclaimer, the term of this patent is extended or adjusted under 35 U.S.C. 154(b) by 132 days.

(21) Appl. No.: 17/878,409

(22) Filed: Aug. 1, 2022

(65) Prior Publication Data

US 2023/0053321 A1 Feb. 16, 2023

Related U.S. Application Data

(60) Provisional application No. 63/228,401, filed on Aug. 2, 2021.

(51) Int. Cl.
*C07D 235/12* (2006.01)
*C02F 5/12* (2023.01)
*C07D 401/04* (2006.01)
*C23F 11/04* (2006.01)
*C23F 11/14* (2006.01)

(52) U.S. Cl.
CPC ......... *C07D 401/04* (2013.01); *C07D 235/12* (2013.01); *C23F 11/149* (2013.01)

(58) Field of Classification Search
CPC ... C07D 401/04; C07D 235/12; C23F 11/149; C23F 11/04; C02F 5/12
See application file for complete search history.

(56) References Cited

U.S. PATENT DOCUMENTS

| | | | |
|---|---|---|---|
| 4,987,186 | A | 1/1991 | Akiyama et al. |
| 4,987,228 | A | 1/1991 | Cantatore et al. |
| 5,000,835 | A | 3/1991 | Taylor et al. |
| 5,213,680 | A | 5/1993 | Kremer et al. |
| 5,314,672 | A | 5/1994 | Vasil |
| 7,264,786 | B2 | 9/2007 | Pakulski et al. |
| 7,438,877 | B2 | 10/2008 | Salma et al. |
| 7,495,045 | B2 | 2/2009 | Buras et al. |
| 7,645,820 | B2 | 1/2010 | Buras et al. |
| 7,713,345 | B2 | 5/2010 | Maldonado et al. |
| 8,153,705 | B2 | 4/2012 | Gillard et al. |
| 8,202,922 | B2 | 6/2012 | Bolel et al. |
| 8,211,294 | B1 | 7/2012 | Zaid et al. |
| 8,241,491 | B1 | 8/2012 | Zaid et al. |
| 8,246,813 | B2 | 8/2012 | Compton et al. |
| 8,734,637 | B2 | 5/2014 | Taylor |
| 9,150,707 | B2 | 10/2015 | Schroeder |
| 9,610,535 | B2 | 4/2017 | Boday et al. |
| 9,932,478 | B2 | 4/2018 | Mouazen et al. |
| 2005/0153846 | A1 | 7/2005 | Gatlin |
| 2005/0238556 | A1 | 10/2005 | Pakulski et al. |
| 2006/0116450 | A1 | 6/2006 | Buras |
| 2008/0090945 | A1 | 4/2008 | Langrick et al. |
| 2009/0097881 | A1 | 4/2009 | Kondoh et al. |
| 2009/0145330 | A1 | 6/2009 | Draper et al. |
| 2009/0149577 | A1 | 6/2009 | Butler et al. |
| 2009/0206003 | A1 | 8/2009 | Draper |
| 2011/0022055 | A1 | 1/2011 | Quintin et al. |
| 2011/0160355 | A1 | 6/2011 | Martin |
| 2011/0306729 | A1 | 12/2011 | Dreessen et al. |
| 2012/0017503 | A1 | 1/2012 | Riggs et al. |
| 2014/0171721 | A1 | 6/2014 | Bertrand, III |
| 2014/0209304 | A1 | 7/2014 | Reed et al. |
| 2015/0104579 | A1 | 4/2015 | Hedrick et al. |
| 2015/0218342 | A1 | 8/2015 | Martin |
| 2015/0360173 | A1 | 12/2015 | Boday et al. |
| 2016/0289450 | A1 | 10/2016 | Mouazen et al. |
| 2016/0348252 | A1* | 12/2016 | Rane .................... C23F 11/149 |
| 2017/0015811 | A1 | 1/2017 | Martin et al. |
| 2017/0022109 | A1 | 1/2017 | Poland et al. |
| 2017/0260095 | A1 | 9/2017 | Song et al. |

(Continued)

FOREIGN PATENT DOCUMENTS

| | | |
|---|---|---|
| AR | 059003 | 3/2008 |
| CN | 102618202 | 8/2012 |

(Continued)

OTHER PUBLICATIONS

International Search Report and Written Opinion for International Application No. PCT/US 2022/039051, mailed Oct. 27, 2022.
Fan Zhang et al., "Performance and theoretical study on corrosion inhibition of 2-(4-pyridyl)-benzimidazole for mild steel in hydrochloric acid", Corrosion Science, vol. 61, (Aug. 2012), pp. 1-9.
Anonymous. "The Use and Performance of Asphalt Binder Modified with Polyphosphoric Acid (PPA)," TechBrief FHWA-HIF-12-030, Mar. 2012, 7 pages.
April, et al. "Polyphosphoric Acid Modification of Asphalt Binders, A Workshop," Apr. 7-8, 2009, Minneapolis, MN, Transportation Research Circular E-C160. URL: http://onlinepubs.trb.org/onlinepubs/circulars/ec160.pdf, retrieved from Internet on Mar. 4, 2015, 174 pages.
Bakke, et al. "Hydrolysis of 1,3,5-Tris(2-hydroxyethyl)hexahydro-s-triazine and Its Reaction with H 2 S," Industrial & Engineering Chemistry Research, 40(26), (2001), pp. 6051-6054.

(Continued)

*Primary Examiner* — Clinton A Brooks
*Assistant Examiner* — Kendall Nicole Heitmeier
(74) *Attorney, Agent, or Firm* — Eric D. Babych; Barnes & Thornburg LLP

(57) ABSTRACT

2-substituted benzimidazoles and methods of preparing the same are disclosed. The compositions may include a compound or salt thereof, a strong acid, and a carboxylic acid. The compositions may exclude a polar aprotic solvent. The compositions may be used to inhibit corrosion of a metal surface in contact with an aqueous system, and provide enhanced protection against corrosion of metals in the aqueous system.

9 Claims, No Drawings

(56) References Cited

U.S. PATENT DOCUMENTS

| | | | |
|---|---|---|---|
| 2017/0306129 A1 | 10/2017 | Song et al. | |
| 2018/0100096 A1 | 4/2018 | Wylde | |
| 2018/0163021 A1 | 6/2018 | Tong et al. | |
| 2018/0163050 A1 | 6/2018 | Mouazen et al. | |

FOREIGN PATENT DOCUMENTS

| | | | | | |
|---|---|---|---|---|---|
| CN | 103333116 | A | * | 10/2013 | |
| CN | 104031355 | | | 9/2014 | |
| CN | 105073943 | B | | 9/2018 | |
| EP | 0636675 | A2 | | 2/1955 | |
| EP | 0121377 | A1 | | 10/1984 | |
| EP | 2262856 | | | 12/2010 | |
| EP | 3121231 | | | 1/2017 | |
| EP | 3710436 | A1 | | 9/2020 | |
| GB | 2306171 | | | 4/1997 | |
| KR | 1462545 | | | 11/2014 | |
| WO | WO 1992/001481 | A1 | | 2/1992 | |
| WO | WO 1999/058600 | A1 | | 11/1999 | |
| WO | WO 2015/007115 | A1 | | 5/2015 | |
| WO | WO 2015/116864 | A1 | | 8/2015 | |
| WO | WO 2015/123329 | A1 | | 8/2015 | |
| WO | 2016191672 | A1 | | 12/2016 | |
| WO | WO 2017/120430 | A1 | | 7/2017 | |
| WO | WO 2018/122680 | A1 | | 7/2018 | |
| WO | WO-2019094672 | A1 | * | 5/2019 | ........... C07D 235/18 |

OTHER PUBLICATIONS

International Preliminary Report on Patentability, PCT/US2020/019866, issued Aug. 25, 2021, 16 pages.

International Search Report and Written Opinion for related International Application No. PCT/US2015/015461, mailed May 22, 2015 (8 pages).

International Search Report and Written Opinion for related International Application No. PCT/US2017/063760, mailed Feb. 23, 2018 (14 pages).

Kodrat, et al. "Comparison of Polyphosphoric Acid-Modified Asphalt Binders with Straight and Polymer-Modified Materials," Transportation Research Record 1998(1), (2007), pp. 47-55.

Lin et al. "Performance characteristics of Terminal Blend rubberized asphalt with SBS and polyphosphoric acid," Construction and Building Materials, 141, (2017), pp. 171-182.

Liu et al. "Laboratory performance of warm mix asphalt binder containing polyphosphoric acid," Construction and Building Materials, 106, (2016), pp. 218-227.

Pankralov, V.A., et al., "Polytriazines," Russian Chemical Reviews, 41(1), pp. 66-82 (1972).

Platonov, V.A. "Properties of Polyphosphoric Acid," Fibre Chemistry, 32(5), (2000), pp. 325-329.

Polacco, et al. "A review ofthe fundamentals of polymer-modified asphalts: Asphalt/polymer interactions and principles of compatibility," Advances in Colloid and Interface Science, 224, (2015), pp. 72-112.

Zhang, et al. "The research for SPS and SBR compound modified asphalts with polyphosphoric acid and sulfur," Construction and Building Materials, 43, (2013), pp. 461-468.

* cited by examiner

ONE-POT HOMOGENEOUS PROCESS FOR THE LARGE SCALE MANUFACTURE OF 2-SUBSTITUTED BENZIMIDAZOLES

BACKGROUND

1. Field of the Invention

The present disclosure generally relates to the synthesis of 2-substituted benzimidazoles and compositions thereof. More particularly, the disclosure pertains to a homogenous process for synthesizing 2-substituted benzimidazoles and their use, for example, as corrosion inhibitors.

2. Description of the Related Art

Benzimidazoles can be made using different synthetic pathways. One common pathway is an acid catalyzed condensation reaction between a diamine and a carboxylic acid. This pathway is mainly focused towards obtaining solid benzimidazoles as isolated final products in moderate to good yields.

These benzimidazoles are predominantly synthesized in mineral acids, and the final product is precipitated by adjusting the pH to 7 or 8 using a base. The precipitated product is isolated by filtration and dried in an oven. Prior art synthetic methods suffer from several disadvantages, such as: 1) prolonged reaction and process times resulting in low throughput per batch; 2) yield loss from workup and isolation steps; 3) isolation and subsequent drying steps require installation of special equipment, thereby incurring a significant capital investment; 4) handling of solid product, both as a wetcake and as dry powder, involves significant material handling challenges resulting in yield loss; and 5) final solid product needs to be dried prior to re-dissolution in a solvent for use in certain applications, such as anti-corrosion.

Other uses for benzimidazoles include applications in pharmaceuticals and agrochemicals. Polybenzimidazoles are known for their high strength and high temperature performance. Polybenzimidazoles find use in semiconductors, contact seals, wafer carriers, insulator bushings, thermal insulators, light emitting diodes, solar cells, fuel cells, and high performance protective apparel. Other uses include applications in the petrochemical and aerospace industries.

BRIEF SUMMARY

In some embodiments, the present disclosure provides compositions comprising a strong acid, a carboxylic acid, and a compound or salt thereof of formula (I):

(I)

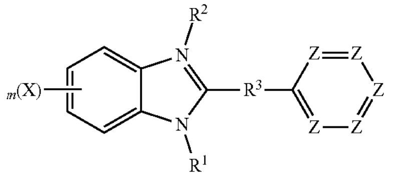

wherein X is independently hydrogen, halogen, or a substituted or unsubstituted $C_{1-5}$ alkyl group, and m is 1, 2, 3, or 4;

$R^1$ is hydrogen, a substituted or unsubstituted $C_1$-$C_{12}$ alkyl group, or a substituted or unsubstituted $C_4$-$C_6$ aryl group;

$R^2$ is absent, hydrogen, a substituted or unsubstituted $C_1$-$C_{12}$ alkyl group, or a substituted or unsubstituted $C_4$-$C_6$ aryl group;

$R^3$ is a bond or $CHR^4$;

$R^4$ is hydrogen, halogen, $NR^5R^6$, or $OR^5$;

wherein $R^5$ and $R^6$ are each independently hydrogen, a substituted or unsubstituted $C_1$-$C_{12}$ alkyl group, or a substituted or unsubstituted $C_4$-$C_6$ aryl group; and Z is independently selected from substituted or unsubstituted C, substituted or unsubstituted N, or any combination thereof, further wherein the composition excludes a polar aprotic solvent.

In some embodiments, the composition further comprises water.

In some embodiments, X is independently hydrogen or halogen; $R^1$ is hydrogen; $R^2$ is absent; and $R^3$ is $CHR^4$.

In some embodiments, $R^3$ is a bond and at least one Z is nitrogen.

In some embodiments, the compound or salt thereof is of formula (II)

(II)

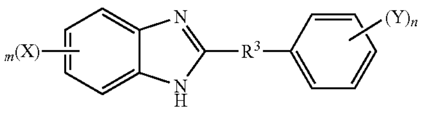

wherein Y is independently hydrogen, halogen, or a $C_{1-5}$ alkyl group; and n is 1, 2, 3, 4, or 5.

In some embodiments, the strong acid is selected from the group consisting of sulfuric acid, hydrochloric acid, nitric acid, methanesulfonic acid, sulfamic acid, p-toluenesulfonic acid, hydrobromic acid, and any combination thereof.

In some embodiments, the carboxylic acid is selected from the group consisting of formic acid, acetic acid, propionic acid, oxalic acid, malic acid, citric acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, and any combination thereof.

In some embodiments, the composition comprises at least about 10 wt. % of the carboxylic acid.

In some embodiments, the composition comprises a high temperature stable phase transfer catalyst.

In some embodiments, the carboxylic acid is acetic acid.

The present disclosure also provides processes for making a compound or salt thereof of formula (V), comprising:

(V)

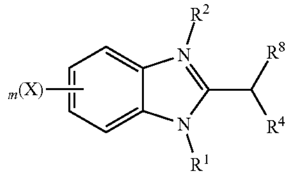

heating a mixture comprising a compound or salt thereof of formula (III), a compound or salt thereof of formula (IV), a strong acid, a carboxylic acid, and a high temperature stable phase transfer catalyst, wherein the mixture excludes a polar aprotic solvent (III)

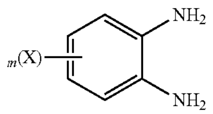

(IV)

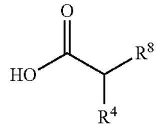

wherein X is independently hydrogen, halogen, or a $C_{1-5}$ alkyl group, and m is 1, 2, 3, or 4;

$R^1$ is hydrogen, a substituted or unsubstituted $C_1$-$C_{12}$ alkyl group, a substituted or unsubstituted $C_4$-$C_6$ aryl group;

$R^2$ is absent, hydrogen, a substituted or unsubstituted $C_1$-$C_{12}$ alkyl group, a substituted or unsubstituted $C_4$-$C_6$ aryl group;

$R^4$ is hydrogen, halogen, $NR^5R^6$, or $OR^5$;

wherein $R^5$ and $R^6$ are each independently hydrogen, a substituted or unsubstituted $C_1$-$C_{12}$ alkyl group or a substituted or unsubstituted $C_4$-$C_6$ aryl group; and $R^8$ is hydrogen, halogen, a substituted or unsubstituted $C_1$-$C_{12}$ alkyl group, a substituted or unsubstituted $C_5$-$C_6$ heteroaryl group, a substituted or unsubstituted $C_4$-$C_6$ aryl group, or a substituted or unsubstituted $C_3$-$C_{12}$ cycloalkyl group, wherein the process excludes a polar aprotic solvent.

In some embodiments, the strong acid is selected from the group consisting of sulfuric acid, hydrochloric acid, nitric acid, methanesulfonic acid, sulfamic acid, p-toluenesulfonic acid, hydrobromic acid, and any combination thereof.

In some embodiments, the carboxylic acid is selected from the group consisting of formic acid, acetic acid, propionic acid, oxalic acid, malic acid, citric acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, and any combination thereof.

In some embodiments, the mixture comprises at least about 10 wt. % of the carboxylic acid.

In some embodiments, the mixture is heated to a temperature of from about 80° C. to about 160° C.

The present disclosure also provides processes for preparing a polybenzimidazole, comprising heating a mixture comprising diphenyl isophthalate and 3,3',4,4'-tetraaminodiphenyl, a strong acid, a carboxylic acid, and a high temperature stable phase transfer catalyst, wherein the process excludes a polar aprotic solvent.

In some embodiments, the strong acid is selected from the group consisting of sulfuric acid, hydrochloric acid, nitric acid, methanesulfonic acid, sulfamic acid, p-toluenesulfonic acid, hydrobromic acid, and any combination thereof.

In some embodiments, the carboxylic acid is selected from the group consisting of formic acid, acetic acid, propionic acid, oxalic acid, malic acid, citric acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, and any combination thereof.

In some embodiments, the mixture comprises at least about 10 wt. % of the carboxylic acid.

The present disclosure also provides methods of inhibiting corrosion, comprising adding the composition of claim 1 to an industrial water system comprising a metallic surface.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION

Various embodiments are described below. The relationship and functioning of the various elements of the embodiments may better be understood by reference to the following detailed description. However, embodiments are not limited to those illustrated below. In certain instances, details may have been omitted that are not necessary for an understanding of embodiments disclosed herein.

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like.

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Huckel's Rule.

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups, such as methyl groups, ethyl groups, and the like.

"Halogen" or "halo" refers to F, Cl, Br, and I.

"Heteroaryl" refers to a monocyclic or bicyclic 5- or 6-membered ring system, wherein the heteroaryl group is unsaturated and satisfies Huckel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like.

"Oxo" refers to an oxygen atom double-bonded to a carbon atom.

Compounds of the present disclosure may be substituted with suitable substituents. The term "suitable substituent," as used herein, is intended to mean a chemically acceptable functional group, preferably a moiety that does not negate the activity of the compounds. Such suitable substituents include, but are not limited to, halo groups, perfluoroalkyl groups, perfluoro-alkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxy-carbonyl groups, alkylsulfonyl groups, and arylsulfonyl groups. In some embodiments, suitable substituents may include halogen, an unsubstituted $C_1$-$C_{12}$ alkyl group, an unsubstituted $C_4$-$C_6$ aryl group, or an unsubstituted alkoxy group. Those skilled in the art will appreciate that many substituents can be substituted by additional substituents.

As used herein, the term "high temperature stable phase transfer catalyst" refers to a phase transfer catalyst that remains stable at the temperatures and conditions required by the methods and processes described herein, particularly as they relate to preparing the compositions described herein. The term "remains stable", in this context, means that the phase transfer catalyst does not decompose or degrade and remains operationally functional at the temperatures and conditions described herein. In some embodiments, the high temperature stable phase transfer catalysts disclosed herein can be stable at temperatures in excess of about 80° C. to in excess of about 250° C. For example, in certain embodiments, the high temperature stable phase transfer catalysts disclosed herein can remain stable at temperatures in excess of about 80° C., about 90° C., 100° C., about 110° C., about 120° C., about 130° C., about 140° C., about 150° C., about 160° C., about 170° C., about 180° C., about 190° C., about 200° C., about 210° C., about 220° C., about 230° C., about 240° C., or about 250° C.

In some embodiments, a composition is disclosed that may include a compound or salt thereof of formula (I), a strong acid and a carboxylic acid. The composition may exclude a solvent. In some embodiments, the composition excludes a polar solvent. In some embodiments, the composition excludes an aprotic solvent. In some embodiments, the composition excludes a polar aprotic solvent. The compound of formula (I) has the formula shown below (I)

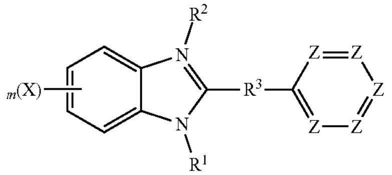

In some embodiments, X is independently hydrogen, halogen, or a substituted or unsubstituted $C_{1-5}$ alkyl group, and m may be 1, 2, 3, or 4. In some embodiments, $R^1$ may be hydrogen, a substituted or unsubstituted $C_1$-$C_{12}$ alkyl group, or a substituted or unsubstituted $C_4$-$C_6$ aryl group. In some embodiments, $R^2$ may be absent, hydrogen, a substituted or unsubstituted $C_1$-$C_{12}$ alkyl group, or a substituted or unsubstituted $C_4$-$C_6$ aryl group. In some embodiments, $R^3$ may be a bond or $CHR^4$. In some embodiments, $R^4$ may be hydrogen, halogen, $NR^5R^6$, or $OR^5$. In some embodiments, $R^5$ and $R^6$ are each independently hydrogen, a substituted or unsubstituted $C_1$-$C_{12}$ alkyl group, or a substituted or unsubstituted $C_4$-$C_6$ aryl group.

If $R^2$ is present, then a counterion may be included. Counterions may include halides, such as chloride, bromide, and iodide, or other counterions, such as methanesulfonate, sulfate, acetate, and formate, for example.

The X substituent or substituents can occupy any available position on the benzimidazole ring. Thus, in certain embodiments, the X substituent or substituents can be located at the 4-position, 5-position, 6-position, and/or 7-position of the benzimidazole. In certain embodiments, the X substituent is at the 5-position.

The number of X substituents, m, can be 1, 2, 3, or 4. If m is 2, 3, or 4, the X substituents can occupy any open position and can be positioned ortho-, meta-, or para- to each other.

In certain embodiments, the salt of the compound of formula (I) may be any salt, such as a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In some embodiments, salt of the compound of formula (I) may be a hydrochloride or sulfate salt.

In some embodiments, Z is independently selected from substituted or unsubstituted C, substituted or unsubstituted N, or any combination thereof.

In some embodiments, Z is CH or N.

In some embodiments, X is hydrogen and m is 4.

In some embodiments, $R^1$ is hydrogen.

In some embodiments, $R^2$ is absent.

In some embodiments, $R^3$ is a bond.

In some embodiments, $R^3$ is $CHR^4$.

In some embodiments, $R^4$ is hydrogen.

In some embodiments, $R^4$ is halogen.

In some embodiments, $R^4$ is $NR^5R^6$.

In some embodiments, $R^4$ is $OR^5$.

In some embodiments, $R^5$ is a substituted or unsubstituted $C_1$-$C_{12}$ alkyl group.

In some embodiments, $R^5$ is hydrogen.

In some embodiments, $R^5$ is a substituted or unsubstituted $C_4$-$C_6$ aryl group.

In some embodiments, one Z is N and the rest are CH. In some embodiments, at least two Zs are N and the rest are CH. In some embodiments, at least three Zs are N and the rest are CH. In some embodiments, at least four Zs are N and the rest are CH. In some embodiments, all Zs are N or all Zs are CH.

In some embodiments, $R^3$ is a bond and at least one Z is N.

In some embodiments, X is independently hydrogen or halogen, $R^1$ is hydrogen, $R^2$ is absent, and $R^3$ is $CHR^4$.

In some embodiments, the compound or salt thereof of formula (I) is

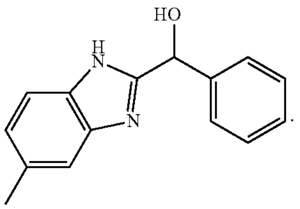 [SMILES: Cc1ccc2[nH]c(C(O)c3ccccc3)nc2c1]

In some embodiments, the compound or salt thereof of formula (I) is

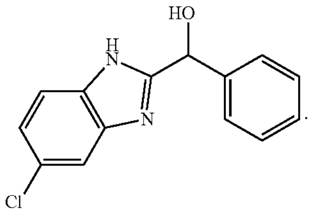 [SMILES: OC(c1ccccc1)c1nc2cc(Cl)ccc2[nH]1]

In some embodiments, the compound or salt thereof of formula (I) is

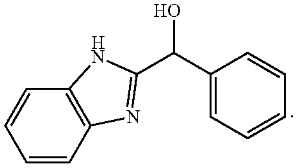 [SMILES: OC(c1ccccc1)c1nc2ccccc2[nH]1]

In some embodiments, the compound or salt thereof of formula (I) is

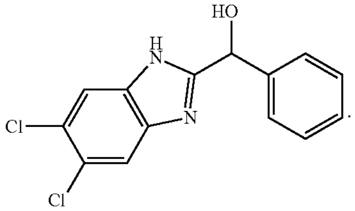 [SMILES: OC(c1ccccc1)c1nc2cc(Cl)c(Cl)cc2[nH]1]

In some embodiments, the compound or salt thereof of formula (I) is

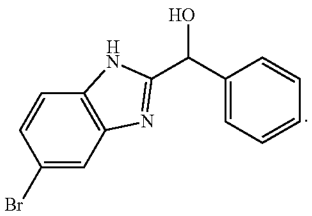 [SMILES: OC(c1ccccc1)c1nc2cc(Br)ccc2[nH]1]

In some embodiments, the compound or salt thereof of formula (I) is

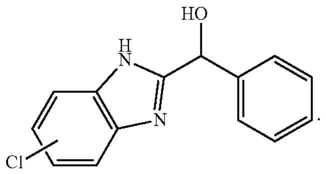

In some embodiments, the compound or salt thereof of formula (I) is

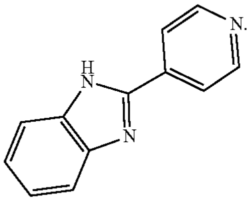 [SMILES: c1ccc2[nH]c(-c3ccncc3)nc2c1]

In some embodiments, the compound or salt thereof of formula (I) is

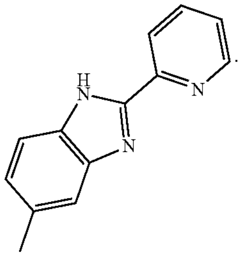 [SMILES: Cc1ccc2[nH]c(-c3ccccn3)nc2c1]

In some embodiments, the compound or salt thereof of formula (I) is

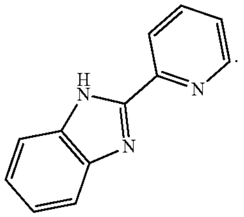 [SMILES: c1ccc(-c2nc3ccccc3[nH]2)nc1]

In some embodiments, the compound or salt thereof of formula (I) is

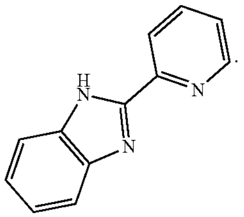 [SMILES: c1ccc(-c2nc3ccccc3[nH]2)nc1]

In some embodiments, the compound or salt thereof of formula (I) is

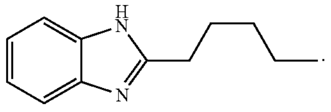

In some embodiments, the compound or salt thereof of formula (I) is

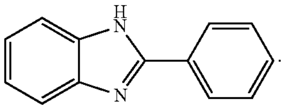 [SMILES: c1ccc(-c2nc3ccccc3[nH]2)cc1]

In some embodiments, the composition may include a compound or salt thereof of formula (Ia), (Ia)

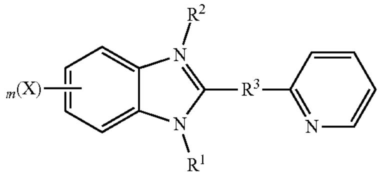

where X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; and $R^3$ is a bond or $CHR^4$.

In some embodiments, the compound or salt thereof is of formula (II), (II)

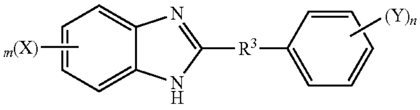

where X, m, and $R^3$ X is independently hydrogen, halogen, or a substituted or unsubstituted $C_{1-5}$ alkyl group; m is 1, 2, 3, or 4; $R^3$ is a bond or $CHR^4$; Y is independently hydrogen, halogen, or a $C_{1-5}$ alkyl group; and n is 1, 2, 3, 4, or 5.

In some embodiments, Y is hydrogen.

In some embodiments, Y is independently hydrogen and halogen.

As described herein, m can be 1, 2, 3, or 4. If m is 2, 3, or 4, the X substituents can occupy any open position and can be positioned ortho-, meta-, or para- to each other. The number of Y substituents, n, can be 1, 2, 3, or 4. If n is 2, 3, or 4, the Y substituents can occupy any open position and can be positioned ortho-, meta-, or para- to each other.

In some embodiments, the concentration of the compound or salt thereof of formula (I), formula (Ia), or formula (II) in the composition may range from about 1 wt % to about 50 wt %, about 5 wt % to about 50 wt %, about 10 wt % to about 50 wt %, about 15 wt % to about 50 wt %, about 20 wt % to about 50 wt %, about 20 wt % to about 45 wt %, about 25 wt % to about 45 wt %, or about 25 wt % to about 40 wt %.

In some embodiments, the strong acid may be a strong inorganic acid, a strong organic acid, or any combination thereof. In some embodiments, the strong acid is a strong inorganic acid. In some embodiments, the strong acid is a strong organic acid. As used herein, "strong" refers to acids having a pKa of less than about 1.

In some embodiments, the strong acid may be selected from the group consisting of sulfuric acid, hydrochloric acid, nitric acid, methanesulfonic acid, sulfamic acid, p-toluenesulfonic acid, hydrobromic acid, and any combination thereof.

In some embodiments, the strong acid may be sulfuric acid.

In some embodiments, the strong acid may be hydrochloric acid.

In some embodiments, the strong acid may be nitric acid.

In some embodiments, the strong acid may be methanesulfonic acid.

In some embodiments, the strong acid may be sulfamic acid.

In some embodiments, the strong acid may be p-toluenesulfonic acid.

In some embodiments, the strong acid may be hydrobromic acid.

The amount of strong acid in the composition may range from about 10 wt. % to about 80 wt. %. For example, the amount of strong acid in the composition may range from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 10 wt. % to about 20 wt. %, from about 15 wt. % to about 20 wt. %, from about 15 wt. % to about 25 wt. %, or from about 15 wt. % to about 30 wt. %.

As used herein, "carboxylic acid" refers to an organic compound that contains a carboxyl group. In some embodiments, the carboxylic acid may be a substituted or unsubstituted $C_1$-$C_{32}$ alkyl carboxylic acid.

In some embodiments, the carboxylic acid is selected from the group consisting of formic acid, acetic acid, propionic acid, oxalic acid, malic acid, citric acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, and any combination thereof.

In some embodiments, the carboxylic acid is acetic acid.

In some embodiments, the composition comprises greater than 5 wt. % of the carboxylic acid, such as at least about 6 wt. %, at least about 7 wt. %, at least about 8 wt. %, at least about 9 wt. % or at least about 10 wt. % of the carboxylic acid. In some embodiments, the composition comprises greater than 10 wt. % of the carboxylic acid. In some embodiments, the composition comprises greater than 12 wt. % of the carboxylic acid. In some embodiments, the composition comprises greater than 15 wt. % of the carboxylic acid. In some embodiments, the composition comprises greater than 5 wt. % of the carboxylic acid, such as at least about 6 wt. %, at least about 7 wt. %, at least about 8 wt. %, at least about 9 wt. %, at least about 10 wt. %, 12 wt. % or 15 wt. % of the carboxylic acid to about 70 wt. %, about 60 wt. %, about 50 wt. %, about 40 wt. %, about 30 wt. % or about 20 wt. % of the carboxylic acid. In some embodiments, the composition comprises greater than 10 wt. % of the carboxylic acid to about 70 wt. % of the carboxylic acid.

In some embodiments, the composition comprises at least about 10 wt. % of the carboxylic acid to about 50 wt. % of the carboxylic acid. In some embodiments, the composition comprises greater than 10 wt. % of the carboxylic acid to about 50 wt. % of the carboxylic acid. In some embodiments, the composition comprises at least about 10 wt. % of the carboxylic acid to about 40 wt. % of the carboxylic acid. In some embodiments, the composition comprises greater than 10 wt. % of the carboxylic acid to about 40 wt. % of the carboxylic acid. In some embodiments, the composition comprises at least about 10 wt. % of the carboxylic acid to about 30 wt. % of the carboxylic acid. In some embodiments, the composition comprises greater than 10 wt. % of the carboxylic acid to about 30 wt. % of the carboxylic acid. In some embodiments, the composition comprises at least about 10 wt. % of the carboxylic acid to about 20 wt. % of the carboxylic acid. In some embodiments, the composition comprises greater than 10 wt. % of the carboxylic acid to about 20 wt. % of the carboxylic acid.

The present inventors unexpectedly discovered that by excluding a solvent, such as a polar solvent, an aprotic solvent, and/or a polar aprotic solvent and including a carboxylic acid, such as acetic acid, the overall stability of the formulation was not adversely affected. By excluding the aforementioned solvent, the formulation also showed an improved environmental profile. Extensive experimentation was carried out to determine that carboxylic acid present in an amount of greater than 5 weight %, such as at least about 10 weight %, achieves the desired low temperature (Freeze-Thaw) stability in addition to other advantages.

The compositions disclosed herein may exclude solvents, polar solvents, aprotic solvents, and/or polar aprotic solvents and any method step disclosed herein may exclude the addition of a solvent, polar solvent, aprotic solvent, and/or polar aprotic solvent. Examples of polar aprotic solvents include acetonitrile, N,N-dimethylformamide, acetone, dimethylsulfoxide, sulfolane, N-methylpyrrolidinone, methylsulfonylmethane, chlorobenzene, o-dichlorobenzene, nitromethane, and ionic liquids. Any of these polar aprotic solvents or any other polar aprotic solvents may be excluded from the compositions and method steps disclosed herein.

In some embodiments, the composition may include a high temperature stable phase transfer catalyst.

In some embodiments, the high temperature stable phase transfer catalyst is selected from the group consisting of an alkyl guanidinium salt, an aryl guanidinium salt, an alkyl phosphonium salt, an aryl phosphonium salt, a peralkylated phosphazenium salt, and any combination thereof. Examples of high temperature stable phase transfer catalysts include, but are not limited to, hexaethyl guanidinium chloride, tetraphenyl phosphonium bromide, hexaalkyl phosphonium salts, hexadecyltributylphosphonium bromide, or any combinations thereof.

In some embodiments, the composition may include water. For example, the composition may comprise from about 5 wt. % to about 95 wt. % water, such as about 5 wt. % to about 50 wt. %, about 5 wt. % to about 25 wt. %, about 10 wt. % to about 50 wt. %, or about 20 wt. % to about 75 wt. % water.

In some embodiments, the composition may be a homogenous mixture. In some embodiments, the composition may be a solution.

In some embodiments, the composition may include a phenylenediamine compound. If the composition includes a phenylenediamine compound, it is present in the composition in an amount of about 0.0001 wt % to about 0.1 wt %. In some embodiments, the amount of phenylenediamine compound in the composition may be less than about 0.1 wt %. In some embodiments, the amount of phenylenediamine compound in the composition may be less than about 0.9 wt %, about 0.8 wt %, about 0.7 wt %, about 0.6 wt %, about 0.5 wt %, about 0.4 wt %, or about 0.3 wt %.

In other embodiments, a process for making a compound or salt thereof of formula (V) is disclosed.

(V)

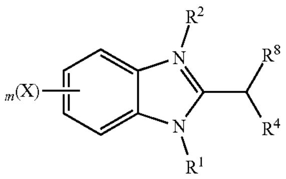

The process may include heating a mixture that includes a compound or salt thereof of formula (III), a compound or salt thereof of formula (IV), a strong acid, a carboxylic acid and a high temperature stable phase transfer catalyst. The process may exclude adding a polar solvent, an aprotic solvent, and/or a polar aprotic solvent.

(III)

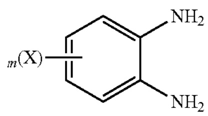

(IV)

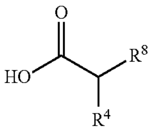

For formulas (III-V), X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^4$ is hydrogen, halogen, $NR^5R^6$, or $OR^5$; and $R^8$ may be hydrogen, halogen, a substituted or unsubstituted $C_1$-$C_{12}$ alkyl group, a substituted or unsubstituted $C_5$-$C_6$ heteroaryl group, a substituted or unsubstituted $C_4$-$C_6$ aryl group, or a substituted or unsubstituted $C_3$-$C_{12}$ cycloalkyl group. $R^5$ and $R^6$ are each independently hydrogen, a substituted or unsubstituted $C_1$-$C_{12}$ alkyl group, or a substituted or unsubstituted $C_4$-$C_6$ aryl group.

In some embodiments, $R^8$ is a substituted or unsubstituted $C_5$-$C_6$ heteroaryl group.

In some embodiments, $R^8$ is a substituted or unsubstituted $C_5$-$C_6$ heteroaryl group or a substituted or unsubstituted $C_4$-$C_6$ aryl group.

In some embodiments, $R^8$ is a substituted or unsubstituted $C_4$-$C_6$ aryl group.

In some embodiments, $R^8$ is a substituted or unsubstituted $C_6$ heteroaryl group.

In some embodiments, $R^8$ is a substituted or unsubstituted $C_6$ aryl group.

In some embodiments, the reaction product of the compounds of formulae (III) and (IV) may be further reacted in a post-modification step to add substituents other than hydrogen for $R^1$ and substituents for $R^2$.

The synthetic processes disclosed herein have many advantages over the prior art. The final product can be obtained in higher yields as compared to conventional synthesis methods. The final product may also be in a homogeneous liquid form, thereby facilitating product transfer and formulation while minimizing yield losses. Since the final product may be in homogeneous liquid form, solids isolation processes and equipment are no longer required resulting in significant cost reductions.

In certain embodiments, a process for making a compound or salt thereof of formula (I) is disclosed.

(I)

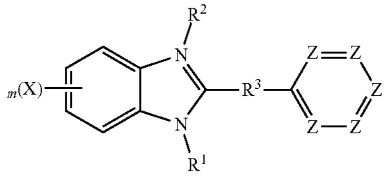

The process may include heating a mixture that includes a compound or salt thereof of formula (III), a compound or salt thereof of formula (VI), a strong acid, a carboxylic acid, and a high temperature stable phase transfer catalyst. The process may exclude adding a polar solvent, an aprotic solvent, and/or a polar aprotic solvent. The mixture may exclude a polar solvent, an aprotic solvent, and/or a polar aprotic solvent.

(III)

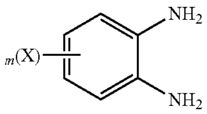

(VI)

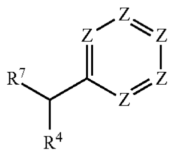

For formulas (I), (III), and (VI), X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^3$ is a bond or $CHR^4$; $R^4$ is hydrogen, halogen, $NR^5R^6$, or $OR^5$, where $R^5$ and $R^6$ are each independently hydrogen, a substituted or unsubstituted $C_1$-$C_{12}$ alkyl group, or a substituted or unsubstituted $C_4$-$C_6$ aryl group; and Z is independently selected from substituted or unsubstituted C, substituted or unsubstituted N, or any combination thereof. In some embodiments, $R^7$ is oxo or COOH.

In some embodiments, $R^7$ is COOH.

In some embodiments, $R^7$ is oxo.

Any acid described in the present disclosure and any equivalents can be used in the process of making compounds or salts of formulas (I) and (V).

In some embodiments, the concentration of the strong acid in the mixture or composition may range from about 10 wt. % to about 80 wt. %. For example, the amount of strong acid may range from about 10 wt. % to about 70 wt. %, from about 10 wt. % to about 60 wt. %, from about 10 wt. % to about 50 wt. %, from about 10 wt. % to about 40 wt. %, from about 10 wt. % to about 30 wt. %, from about 10 wt. % to about 20 wt. %, from about 15 wt. % to about 20 wt. %, from about 15 wt. % to about 25 wt. %, or from about 15 wt. % to about 30 wt. %.

Any high temperature stable phase transfer catalyst described in the present disclosure and any equivalents can be used in the process of making compounds or salts of formulas (I) and (V).

In some embodiments, the concentration of high temperature stable phase transfer catalyst in the mixture or composition may range from about 0.001 wt % to about 30 wt %. In some embodiments, the concentration of high temperature stable phase transfer catalyst in the mixture or composition may range from about 0.001 wt % to about 25 wt %, about 0.001 wt % to about 20 wt %, about 0.01 wt % to about 25 wt %, about 0.1 wt % to about 25 wt %, about 0.5 wt % to about 25 wt %, about 1 wt % to about 25 wt %, about 1 wt % to about 20 wt %, or about 1 wt % to about 25 wt %. In some embodiments, the concentration of polar aprotic solvent in the mixture may be 1 wt %, 5 wt %, or 10 wt %.

In some embodiments, the process of making a compound or salt thereof of formula (I) or (V) may include heating the mixture to a temperature of from about 80° C. to about 160° C. In some embodiments, the mixture may be heated to a temperature of from about 80° C. to about 120° C., about 90° C. to about 120° C., or about 90° C. to about 110° C. The mixture can be heated using any means suitable for raising the temperature to the appropriate level. Heating systems may be fuel-, electricity-, or steam-based. For example, steam could be passed through tubes that contact the mixture.

In some embodiments, the mixture may be heated for a period of time ranging from about 30 minutes to about 12 hours. In some embodiments, the mixture may be heated for a period of time ranging from about 1 hour to about 12 hours, about 2 hours to about 12 hours, about 2 hour to about 10 hours, about 4 hour to about 10 hours, or about 5 hour to about 10 hours.

In some embodiments, the mixture may have an actives concentration of from about 1 to about 50% by weight, where "actives concentration" refers to the concentration of compounds of formula (III) and formula (IV) or compounds of formula (III) and formula (VI). In some embodiments, the mixture may have an actives concentration of from about 10 wt % to about 50 wt %, about 20 wt % to about 50 wt %, about 20 wt % to about 45 wt %, about 25 wt % to about 45 wt %, or about 25 wt % to about 40 wt %.

In some embodiments, a composition is disclosed that is prepared according to the processes described in this disclosure. The processes of making a compound or salt of formula (I) or (V) may produce a homogenous composition that can be used for corrosion inhibition without further purification.

In some embodiments, the compositions of this disclosure can be used in pharmaceuticals. In some embodiments, the compositions of this disclosure can be used in agrochemicals. In some embodiments, the compositions of this disclosure can be used for inhibiting corrosion.

In some embodiments, a method of preventing corrosion is disclosed.

The disclosure provides methods of using heterocyclic compounds and formulations comprising heterocyclic compounds that are particularly useful for inhibiting corrosion of metallic components in industrial water systems. Adding to an aqueous system a benzimidazole capable of undergoing chelation with a metal provides excellent metal corrosion resistance. In particular, adding benzimidazoles substituted with a 2-pyridyl or a benzyl alcohol to an aqueous system in contact with a metal surface leads to excellent corrosion inhibition for metals, such as copper. Moreover, while benzotriazoles and benzimidazoles are generally unstable in the presence of oxidizing halogen compounds, the compounds of the present disclosure are capable of undergoing 1,2-chelation with a metal to impart exemplary protection of metal in the presence of oxidizing halogen compounds. In particular, 2-(2-pyridyl)benzimidazoles provide greater protection against corrosion than benzimidazole, 2-phenylbenzimidazole, and tolyltriazole in the presence of oxidizing halogen compounds. While not wishing to be bound by any particular theory, it is believed that the compounds of the present disclosure form a protective film that is essentially impenetrable by common oxidizing halogen compounds due to bidentate chelation of the corrosion inhibitor with the metal surface. Thus, in certain embodiments, the methods of the present disclosure provide protection against metal corrosion in aqueous systems which employ oxidizing halogen compounds as biocides.

In some embodiments, the disclosure provides a method for inhibiting corrosion of a metal surface in contact with an aqueous system. The method may include adding to the aqueous system any composition described in the present disclosure. For example, the composition may include a compound of formula (I), a strong acid and a carboxylic acid. The composition may exclude a polar aprotic solvent, a polar solvent, and/or an aprotic solvent.

"Industrial water system" means any system that circulates water as its primary ingredient. Non-limiting examples of "industrial water systems" include cooling systems, boiler systems, heating systems, membrane systems, papermaking systems, or any other systems that circulate water.

The compounds of formulae (I), (Ia), and (II) may provide corrosion protection for any metal or metal alloy including, but not limited to, copper, iron, silver, steel (e.g., galvanized steel), and aluminum. In certain embodiments, a compound of formula (I), (Ia), or (II) is added to an aqueous system in contact with a metal surface comprising copper to inhibit metal corrosion. In certain embodiments, a compound of formula (I), (Ia), or (II) is added to an aqueous system in contact with a metal surface comprising a copper alloy to inhibit metal corrosion. In certain embodiments, copper complexes with one or more heteroatoms in a compound of formula (I), (Ia), or (II). In certain embodiments, copper complexes with one or more heteroatoms in a compound of formula (I), (Ia), or (II). Copper has a wide-range of applications, including use as copper piping and tubing in plumbing and industrial machinery. Copper and copper alloys are well known for their use in cooling water and boiler water systems.

The compounds of formulae (I), (Ia), and (II) can be used to protect any copper alloy, including bronze and brass. Bronze commonly comprises copper and tin, but may comprise other elements including aluminum, manganese, silicon, arsenic, and phosphorus. Brass comprises copper and zinc, and is commonly used in piping in water boiler systems. In certain embodiments, a compound of formula (I), (Ia), or (II) is added to an aqueous system in contact with a metal surface comprising bronze to inhibit metal corrosion. In certain embodiments, a compound of formula (I), (Ia), or (II) is added to an aqueous system in contact with a metal surface comprising brass, for example admiralty brass, to inhibit metal corrosion. In certain embodiments, a compound of formula (I), (Ia), or (II) is added to an aqueous system in contact with a metal surface comprising a copper-nickel alloy to inhibit metal corrosion.

In certain embodiments, a compound of formula (I), (Ia), or (II) inhibits the corrosion of mild steel. In certain embodiments, a compound of formula (I), (Ia), or (II) inhibits the corrosion of metal alloys including, but not limited to, galvanized steel, stainless steel, cast iron, nickel, and combinations thereof. While not wishing to be bound by any particular theory, it is postulated that the compounds of formulae (I), (Ia), and (II) inactivate Cu (II) in solution, preventing the occurrence of galvanic cells on the steel surface. Thus, in certain embodiments, a compound of formula (I), (Ia), or (II) inhibits pitting corrosion of mild steel.

While the compounds of formulae (I), (Ia), and (II) can be added to an aqueous system at any dosage rate, the compounds of formulae (I), (Ia), and (II) are generally added to an aqueous system at a dosage rate of from about 0.01 ppm to about 500 ppm. In certain embodiments, a compound of formula (I), (Ia), or (II) is added to an aqueous system at a dosage rate of from about 0.01 ppm to about 100 ppm. In certain embodiments, a compound of formula (I), (Ia), or (II) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

In certain embodiments, the aqueous system is a cooling water system. The cooling water system can be a closed loop cooling water system or an open loop cooling water system. In certain embodiments, a compound of formula (I), (Ia), or (II) is added to a closed loop cooling water system at a dosage rate of from about 0.01 ppm to about 200 ppm. In certain embodiments, a compound of formula (I), (Ia), or (II) is added to an open loop cooling water system at a dosage rate of from about 0.01 ppm to about 20 ppm.

The compounds of formulae (I), (Ia), and (II) are contacted with a metal surface by any suitable method. In certain embodiments, a solution of a compound of formula (I), (Ia), or (II) is contacted with a metal surface by immersion, spraying, or other coating techniques. In certain embodiments, a solution of a compound of formula (I), (Ia), or (II) is introduced into the water of the aqueous system by any conventional method and is fed into the aqueous system on either a periodic or continuous basis.

In some embodiments, the compositions disclosed herein may include a fluorescent organic compound. In certain embodiments, the fluorescent organic compound may be selected from Rhodamine or derivatives thereof, an acridine dye, fluorescein or derivatives thereof, and combinations thereof. In certain embodiments, the compositions disclosed herein may include a fluorescent tagged polymer.

Those skilled in the art will appreciate that a compound of formula (I), (Ia), or (II) can be added to an aqueous system alone or in combination with other corrosion inhibitors or treatment chemicals. Multiple corrosion inhibitors can be dosed as a combined corrosion inhibitor formulation or each corrosion inhibitor can be added separately, including two or more compounds of formula (I), (Ia), and/or formula (II). Moreover, a compound of formula (I), (Ia), or (II) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I), (Ia), and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

In other embodiments, a process for making polybenzimidazoles may include heating a mixture that has diphenyl isophthalate and 3,3',4,4'-tetraaminodiphenyl, a carboxylic acid, a strong acid, and a high temperature stable phase transfer catalyst. The process may exclude the addition of a polar solvent, an aprotic solvent, and/or a polar aprotic solvent. The strong acid, carboxylic acid, and high temperature stable phase transfer catalyst are as described in this disclosure.

Polybenzimidazoles are known for their high strength and high temperature performance. The polybenzimidazoles synthesized according to the processes disclosed herein can be used in, for example, semiconductors, contact seals, wafer carriers, insulator bushings, thermal insulators, light emitting diodes, solar cells, fuel cells, and high performance protective apparel. Other uses include applications in the petrochemical and aerospace industries.

EXAMPLES

Example 1

Methanesulfonic acid and water were charged into a flask fitted with a magnetic stirrer, reflux condenser and a temperature probe. To this, DL-Mandelic acid (1 equiv.) and 1,2-phenylenediamine (1 equiv.) were added and the contents of the flask were refluxed at about 100 to 110° C. for about 6 to 8 hours. After completion of the reaction, acetic acid (about 10 wt. %) was added and maintained the reflux for additional 1 to 3 hours. After the post treat, an additional amount of water was added to adjust the actives to about 20%. Purity and residual OPD analysis was performed using NMR and HPLC. The process resulted in the production of a homogeneous solution.

Example 2

Methanesulfonic acid and water were charged into a flask fitted with a magnetic stirrer, reflux condenser and a temperature probe. To this, DL-Mandelic acid (1 to 1.05 equiv.) and 1,2-phenylenediamine (1 equiv.) were added and the contents of the flask were refluxed at about 100 to about 110° C. for about 6 to about 8 hours. After completion of the reaction, the specified amount of acid was added and reflux was maintained for additional 1 to 3 hours. Then, an additional amount of water was added to adjust the actives to about 20%. Purity and residual OPD analysis was performed using NMR and HPLC.

Samples were subjected to 10 rounds of freeze-thaw stability testing. Each sample was placed in a freezer at about −10° F. and allowed to freeze over a period of 48 hours. The frozen samples were brought to ambient temperature over the next 48 hours until the frozen material was completely thawed. This process was repeated 10 times and the samples were examined for any precipitation. The % actives for all the samples was about 20% with varying amounts of acetic acid (0%, 5%, 10% and 40%) or 10% of a different acid. The results are shown in Table 1.

TABLE 1

Freeze-Thaw stability results (after 10 rounds)

| Entry | Additive | Precipitation |
|---|---|---|
| 1 | 0% Acetic acid | Yes |
| 2 | 5% Acetic acid | Yes |
| 3 | 10% Acetic acid | No |
| 4 | 40% Acetic acid | No |
| 5 | 10% Chloroacetic acid | Yes |
| 6 | 10% Gluconic acid | Yes |
| 7 | 10% Hexanoic acid | Yes |
| 8 | 10% Citric acid | Yes |
| 9 | 10% 6-aminohexanoic acid | Yes |
| 10 | 10% Iminodiacetic acid | Yes |
| 11 | 10% DL-Malic acid | Yes |

As can be seen in Table 1, only about 10 wt. % and about 40 wt. % acetic acid provided homogeneous samples with no noticeable precipitation or crystallization.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a strong acid" is intended to include "at least one strong acid" or "one or more strong acids."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Any composition disclosed herein may comprise, consist of, or consist essentially of any element, component and/or ingredient disclosed herein or any combination of two or more of the elements, components or ingredients disclosed herein.

Any method disclosed herein may comprise, consist of, or consist essentially of any method step disclosed herein or any combination of two or more of the method steps disclosed herein.

The transitional phrase "comprising," which is synonymous with "including," "containing," or "characterized by," is inclusive or open-ended and does not exclude additional, un-recited elements, components, ingredients and/or method steps.

The transitional phrase "consisting of" excludes any element, component, ingredient, and/or method step not specified in the claim.

The transitional phrase "consisting essentially of" limits the scope of a claim to the specified elements, components, ingredients and/or steps, as well as those that do not materially affect the basic and novel characteristic(s) of the claimed invention.

Unless specified otherwise, all molecular weights referred to herein are weight average molecular weights and all viscosities were measured at 25° C. with neat (not diluted) polymers.

As used herein, the term "about" refers to the cited value being within the errors arising from the standard deviation found in their respective testing measurements, and if those errors cannot be determined, then "about" may refer to, for example, within 5% of the cited value.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A composition, comprising: a strong acid, a carboxylic acid, and a compound or salt thereof of formula (I):

(I)

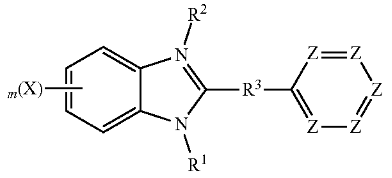

wherein each X is independently hydrogen, halogen, or a $C_{1-5}$ alkyl group, and m is 1, 2, 3, or 4;

$R^1$ is hydrogen, a $C_1$-$C_{12}$ alkyl group, or a $C_4$-$C_6$ aryl group;

$R^2$ is absent, hydrogen, a $C_1$-$C_{12}$ alkyl group, or a $C_4$-$C_6$ aryl group;

$R^3$ is a bond or $CHR^4$;

$R^4$ is hydrogen, halogen, $NR^5R^6$, or $OR^5$;

wherein $R^5$ and $R^6$ are each independently hydrogen, a $C_1$-$C_{12}$ alkyl group, or a $C_4$-$C_6$ aryl group; and each Z is independently selected from CH and N, wherein:

the carboxylic acid is acetic acid, and the composition comprises greater than 10 wt. % to 70 wt. % of the carboxylic acid, and further wherein the composition excludes a polar aprotic solvent.

2. The composition of claim 1, further comprising water.

3. The composition of claim 1, wherein each X is independently hydrogen or halogen;

$R^1$ is hydrogen;

$R^2$ is absent; and $R^3$ is $CHR^4$.

4. The composition of claim 1, wherein $R^3$ is a bond and at least one Z is nitrogen.

5. The composition of claim 1, wherein the compound or salt thereof is of formula (II)

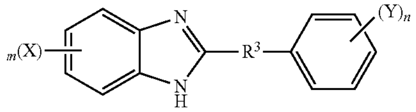

wherein

Y is independently hydrogen, halogen, or a $C_{1-5}$ alkyl group; and n is 1, 2, 3, 4, or 5.

6. The composition of claim 1, wherein the strong acid is selected from the group consisting of sulfuric acid, hydrochloric acid, nitric acid, methanesulfonic acid, sulfamic acid, p-toluenesulfonic acid, hydrobromic acid, and any combination thereof.

7. The composition of claim 1, further comprising a high temperature stable phase transfer catalyst.

8. The composition of claim 1, wherein a concentration of the compound of formula (I), or a salt thereof, in the composition is about 1 wt. % to about 50 wt. %.

9. A method of inhibiting corrosion, comprising:

adding the composition of claim 1 to an industrial water system comprising a metallic surface.

* * * * *